United States Patent [19]

Adcock

[11] Patent Number: 5,248,795
[45] Date of Patent: Sep. 28, 1993

[54] 3-HYDRYL-F-OXETANE AND 3,3-DIHYDRYL-F-OXETANE COMPOUNDS USEFUL AS REFRIGERANTS OR SOLVENTS

[75] Inventor: James L. Adcock, Knoxville, Tenn.

[73] Assignee: Electric Power Research Institute, Palo Alto, Calif.

[21] Appl. No.: 804,796

[22] Filed: Dec. 9, 1991

[51] Int. Cl.$^5$ .......................................... C07D 305/08
[52] U.S. Cl. .................................. 549/510; 549/511
[58] Field of Search ............................. 549/510, 511

[56] References Cited

U.S. PATENT DOCUMENTS

| | | | |
|---|---|---|---|
| 2,594,272 | 4/1952 | Kauck et al. | 260/333 |
| 3,125,581 | 3/1964 | Coffman et al. | 260/333 |
| 4,330,475 | 5/1982 | Adcock et al. | 549/380 |
| 4,855,112 | 8/1989 | Adcock | 422/186 |

FOREIGN PATENT DOCUMENTS 739882 3/1970 Belgium .

Primary Examiner—C. Warren Ivy
Assistant Examiner—Ba K. Trinh
Attorney, Agent, or Firm—Flehr, Hohbach, Test, Albritton & Herbert

[57] ABSTRACT

This invention discloses novel compounds 3-hydryl-F-oxetane and 3,3-dihydryl-F-oxetane, for use as refrigerants or solvents. The compounds will serve as close replacements for CFC's R-11 and R-113.

3 Claims, No Drawings

3-HYDRYL-F-OXETANE AND 3,3-DIHYDRYL-F-OXETANE COMPOUNDS USEFUL AS REFRIGERANTS OR SOLVENTS

This application was made with the support of the U.S. Government under CPA Contract No. 815147-02-0. The Government has certain rights in this invention.

GOVERNMENT SUPPORT

Work relating to this invention was supported by the U.S. Environmental Protection Agency.

FIELD OF THE INVENTION

This invention discloses two new fluorinated oxetane compounds for use as refrigerants or solvents.

BACKGROUND OF THE INVENTION

Chlorinated fluorocarbons (CFCs) are commonly used as refrigerants and solvents with a wide variety of industrial applications. However, with the discovery of significant effect of these compounds on the ozone layer of the Earth's atmosphere it would be environmentally and economically advantageous if replacements for CFCs could be found. Promising replacements for the CFCs would be compounds with very short atmospheric lifespans and absence of chlorine atoms in the compounds, the latter capable of producing free-radicals that disrupt the ozone layer.

Fluorinated oxetanes are compounds the physical properties of which appear to make them exceptionally close replacements for the halogenated CFCs R-114, R-113, and R-11. fluorinated oxetanes contain hydrogen atoms which contribute to their very short atmospheric lifespan, and they do not contain chlorine. Thus, their production and use poses no known threat to the ozone.

SUMMARY OF THE INVENTION

The successful direct fluorination of oxetane, cyclo-$CH_2CH_2CH_2$—O—, has led to the discovery that important new compounds can be produced preferentially to other isomers. A 3-hydryl fluorinated oxetane (cyclo-$CF_2CFHCF_2$—O—) and 3,3-dihydryl fluorinated oxetane (cyclo-$CF_2CH_2CF_2$—O—) have been produced which have properties comparable to those of the CFCs, particularly to $CF_2ClCF_2Cl$ (CFC-114), in the case of the 3-hydryl compound, and to $CFCl_3$ (R-11) and $CF_2ClCFCl_2$ (R-113), in the case of the 3,3-dihydryl compounds, without the attendant environmental problems.

Prior to this invention, only 2,2-dihydryl-F-oxetane could be produced, by the addition of formaldehyde, $CH_2O$, and tetrafluoroethylene, $CF_2=CF_2$. Since the isomers describe herein have not been produced, and likely cannot be produced, by addition or condensation processes, they stand as unique compounds. Although a fully fluorinated oxetane, cyclo-$CF_2CF_2CF_2$—O—, was supported in U.S. Pat. No. 2,594,272.

DETAILED DESCRIPTION OF THE INVENTION

The present invention discloses the successful syntheses of 3-hydryl-F-oxetane and 3,3-dihydryl-F-oxetane by stoichiometrically controlled aerosol direct fluorination of oxetane. Direct fluorination methods and apparatus useful to produce the compounds of this invention are disclosed in U.S. Pat. Nos. 4,330,475 and No. 4,855,112, incorporated herein by reference.

The reaction and the method for producing the fluorinated oxetanes disclosed in this invention depend on the reaction of oxetane with fluorine, preferably in the form of sodium fluoride (NaF) aerosol particulates in the presence of fluorine gas. This reaction need not be carried out in the presence of light activation energy, although preferably it will be conducted in the presence of a UV light source, which drives the reaction toward fully-fluorinated forms of oxetane. Thus, even were the reactants not exposed to light activation energy under the experimental conditions described herein, partially fluorinated oxetanes would be produced.

Alternatively, the reaction may be carried out in the presence of a higher concentration of fluorine gas or NaF, or for a longer period of time, or various other modifications well-known to those skilled in the art of reaction kinetics. This alternative reaction environment may be beneficial if one wishes to isolate relatively higher ratios of 3,3-dihydryl-F-oxetane to 3-hydryl-F-oxetane, as the reaction will not be driven as readily to complete fluorination. However, this environment requires more of an expensive reactant, fluorine or NaF, and so light activation with lower required concentrations of fluorine reactants is presently preferred, at least where the reactants are not recycled.

The presently preferred aerosol fluorination of oxetane is carried out in the following manner. An inert gas, helium, hydrogen, argon or the like, serves as a carrier gas. This carrier gas is passed through an oven in which the temperature is held above the sublimation temperature of a compound used to provide aerosol particulates for the fluorination reaction. Thus, for example, the carrier gas is passed over sublimating NaF, where the temperature of the oven is in the range from about 900° C. to about 1050° C. In the presently preferred embodiment, the temperature of the oven is about 950°-1000° C.

Contact of the sublimating sodium fluoride with the carrier gas results in a highly dispersed sodium fluoride particle/carrier gas stream, to produce an aerosol particulate stream. This aerosol particulate stream is cooled to temperatures in the range of about −150° C. to −200° C. and is introduced via a plurality of nozzles into an aerosol generator, described below.

A second portion of inert carrier gas is used to transport vaporized oxetane to be fluorinated. This portion of carrier gas is passed through an evaporator. The evaporator is supplied with oxetane in liquid form or dissolved in a solvent, which is either inert or produces a readily separable side-product. The evaporator is held at a temperature high enough to evaporate the oxetane. In a preferred embodiment, the temperature of the evaporator is held in the range from about 90° C. to about 100° C. Presently preferred temperatures are in the range from about 95°-96° C.

This oxetane mixture formed by volatilizing the oxetane into the inert carrier gas is then introduced via a heated injector into the aerosol generator containing the aerosol particulate stream. The injector in this case is held at a temperature such that the oxetane does not condense on the aerosol generator components. Preferred temperatures are in the range from about 85° C. to about 90° C. Presently preferred temperatures are in the rang from about 86°-87° C.

The nozzles are adjustable so that flow of the aerosol particulate stream and the stream of oxetane mixture is directed to meet at the focus of the aerosol formation zone in the aerosol generator. The convergence of the two streams is organized so that the oxetane mixture stream flows in a straight line from the injector, past the aerosol generator and into the fluorination chamber, at that point having contacted the aerosol particulate stream. The relative temperatures of the components and the convergence of the two streams causes the oxetane to coalesce on the sodium fluoride particulates in the carrier gas. An oxetane/aerosol particulate mixture is thus formed in this section of the aerosol generator, and is channeled into the fluorination chamber.

In a preferred embodiment, the fluorination chamber or reaction zone is made up of two reaction modules, although reaction modules are preferably unitary components which may be added or subtracted to vary the reaction conditions. The oxetane/aerosol particulate mixture flows into the subambient temperature conditions of the reaction zone. At this stage, a first influx of fluorine gas is provided, setting up a concentration gradient through the rest of the reaction zone wherein the oxetane/aerosol particulate mixture encounters progressively higher fluorine concentrations and progressively higher temperatures as it travels through the reaction modules.

The reaction modules are essentially identical. The modules are designed such that the oxetane/aerosol particulate mixture stream flows through the reaction modules where it contacts fluorine diluted in an inert gas (preferably He), injected at subambient temperatures through microporous elements into the modules, but is not allowed to contact the walls of the reaction module. The reaction modules are preferably cylindrical, and thus it is possible to provide the injected fluorine gas, injected through the microporous elements, to flow at relatively constant flow rate along the sides of the reaction module, protecting the walls with a barrier layer of fluorine diluted in an inert gas from contact with the oxetane/aerosol particulate mixture, while allowing contact of the fluorine gas with the oxetane/aerosol particulate mixture.

Thus, throughout the reaction modules, the oxetane in the oxetane/aerosol particulate mixture is being fluorinated. The preferred flow rate of fluorine will vary with the scale of the reactor, which affects the concentration of fluorine atoms. Thus, in a reactor of the scale demonstrated in the examples, the flow rate of fluorine is about 100-150 cc/min. In the presently preferred embodiment the flow rate of fluorine into the reaction module is about 137 cc/min.

The temperature of the reaction module is important for the fluorination reaction to occur. In a preferred embodiment, the temperature will be in the range from about 0° C. to about −60° C., preferably to about −30° C. In the presently preferred embodiment, the temperature of the first reaction module is about −10° C. and the temperature of the second reaction module is about 9° C. The ratio of replaceable hydrogen to fluorine gas is also crucial. In a preferred embodiment the ratio of replaceable hydrogen to fluorine gas is from about 1:1 hydrogen:fluorine to about 1:5 hydrogen:fluorine. In the presently preferred embodiment, the ratio is about 1:2.65 hydrogen:fluorine.

Fluorine gas and the oxetane/aerosol particulate mixture come into contact in the reaction modules under conditions which cause fluorination of the oxetane. However, the fluorination is generally not complete, and only 40-60% fluorination is achieved to this stage. Thus, at this stage only partially fluorinated oxetane is produced.

In a preferred embodiment, the reactants flow from the final reaction module into a photochemical stage. As discussed hereinabove, these reactions need not be carried out in the presence of light activation energy, although this environment does drive the reaction toward complete fluorination of oxetane. An activating light source in the photochemical stage activates further reaction between fluorine and the partially fluorinated oxetane, to bring about additional fluorination of the partially fluorinated oxetane. It is believed that this photoactivation principally dissociates molecular fluorine.

In a preferred embodiment, the light activation energy is provided by a light source which produces ultraviolet (UV) light, and is positioned vertically below the outflow from the reaction module. Partially fluorinated reactants and fluorine gas from the reaction module flow into a quartz tube, made impermeable to attack by the hydrogen fluoride by a thin (preferably about 10 mil) perfluorinated ethylene-propylene copolymer lining, such as Teflon FEP TM. The quartz tube through which the reactants flow is preferable positioned at one focus of a small ellipse, close enough so the UV light may activate the reactions within the tube, with the UV source at the other focus.

In a preferred embodiment, a reflector is provided to reflect UV light directed away from the quartz tube back toward the tube. At this stage, substantially fluorinated oxetane may be isolated. By substantially fluorinated is meant oxetane with from one to five fluorine atoms attached, preferably with four or five fluorine molecules attached, to produce, respectively, 3,3-dihydryl-F-oxetane and 3-hydryl-F-oxetane.

In a preferred embodiment, the final portion of the reaction apparatus is the product trap. Fluorinated oxetane and other reactants from the photochemical stage flow into the product trap chamber, which having a diameter substantially larger than the diameter of the photochemical stage decreases the flow velocity of the products. The products flow into the chamber and contact sodium fluoride pellets placed on a stage in the chamber. The chamber is cooled to a low temperature, such as by liquid nitrogen. This cooling and the static charge built up on the pellets by the flow of the products across the pellets causes deposition of the aerosol particles onto the sodium fluoride pellets. The remaining gas is passed through appropriate traps to scrub residual hydrogen fluoride and to remove residual elemental fluorine.

To better illustrate the procedures employed and the advantages of the resulting product, the following example is provided, which is not intended to in any way limit the scope of this invention.

EXAMPLES

The aerosol fluorination of oxetane was carried out using the apparatus and method disclosed in U.S. Pat. No. 4,855,112, incorporated herein by reference. The apparatus was used under the following conditions:

Temp. of the oven: 950°-1000° C.
Temp. of the injector: 86°-87° C.
Temp. of the evaporator: 95°-96° C.
Temp. of Reactor Module #2: −9° C.
Temp. of Reactor Module #2: −9° C.

The fluorinated product obtained under these conditions was treated with 20% aqueous sodium carbonate solution for 24 hrs. at room temperature (in a stainless steel cylinder) with occasional shaking. The cylinder was then cooled to about $-10°$ C. or $-15°$ C. and fractionated on the vacuum line with traps cooled to $-45°$ C., $-78°$ C., $131°$ C., and $-196°$ C. The major part of the product was collected in the $-131°$ C. trap.

The product was then subjected to separation on a Bendix gas chromatograph (Stationary phase 13% QF-1 Fluorosilicone, 60–80 mesh on chromsorb.P; Temperature profile: Detector 45° C.; Inlet 45° C.. Column Program: $-10°$ C. for 3 min.; 1.5° C./min. up to 60° C.—2 min.; 5° C./min. up to 120° C.—1 min.).

Depending on the product desired, different experimental conditions may be used in conjunction with the apparatus conditions described above, of which the following are exemplary:

Experiment 1

The following conditions were used when the monohydrogenated oxetane was desired:
UV source: Short UV light (550 Watt; 4.5° long positioned in quartz well).
Ratio of Replaceable Hydrogen:Fluorine Gas- 1:2.65
Total Fluorine: 137 cc/min.
Fluorine Distribution: 9, 75, 47, 6 cc/min.

| Peak # | Characterization: RETENTION TIME* | % | COMPOUND |
|---|---|---|---|
| 1 | 13 min. 15 sec. | 57.0 | F-oxetane |
| 2 | 32 min. 15 sec. | 34.7 | 3-hydroyl-F-oxetane |
| 3 | 45 min. 28 sec | 8.0 | 3,3-dihydryl-F-oxetane |

*Carrier flow = 35 cc/min.

The desired compound, 3-hydryl-F-oxetane, was present in the second fraction and showed the following spectroscopic properties:
Infrared absorption bands appeared at: 3021 75, 1336.51, 1299.23, 1275.95, 1224.60, 1181.73, 1107.04, 990.57, and 907.48 cm$^{-1}$.
F-19 NMR (ppm vs CFCl$_3$; 10% CDCl$_3$) Chemical Shifts:

OCF$_a$F$_b$ $\phi_s$= $-77.50$ pm(d of d); 2F; J$_{ab}$=103.75 Hz; J$_{ac}$=15.95 Hz $\phi_b$= $-88.63$ ppm (d of t); 2F; J$_{ab}$=103.75 Hz; J=12.20 Hz CF$_c$H$_d$ $\phi_c$= $-202.91$ ppm (d of t); 1F; J$_{cd}$=44.7 Hz; J=9.15 Hz H-1 NMR (CDCl$_3$ ppm): CF$_c$H$_d$ $\delta_d$=5.11 ppm (d of t) J$_{cd}$=44.7Hz; J=2.7 Hz Experiment 2

The following conditions were used the dihydrogenated oxetane was desired:
UV Source: Short UV light (550 Watt; 4.5° long in Pyrex well, a 1" wide shade positioned between reactor tube and UV source).
Ratio of Replaceable Hydrogen:Fluorine Gas -1:2.17
Total Fluorine: 112 cc/min.
Distribution of Fluorine: 9 50 47 6 cc/min.

| Peak # | Characterization: RETENTION TIME* | % | COMPOUND |
|---|---|---|---|
| 1. | 6 min. 35 sec. | 15.6 | F-oxetane |
| 2. | 9 min. 55 sec. | 2.2 | |
| 3. | 11 min. 5 sec. | 3.0 | |
| 4. | 15 min. 00 sec. | 50.2 | 3-hydryl-F-oxetane |
| 5. | 26 min. 55 sec. | 17.2 | 3,3-dihydryl-F-oxetane |
| 6. | 30 min. 45 sec. | 11.6 | |

*Carrier flow = 75 cc/min.

The desired compound, 3,3-dihydryl-F-oxetane, was present in fraction five and showed the following spectroscopic properties:
Infrared absorption bands appeared at: 3001.47(w), 1443,86(s), 1302.32(s), 1267.64(s), 1152.92(s), 1137.63(s), 1000.58(s), 979.17(s), 893.06(s), 893.06(s), 829.68(m), 535.39(m), and 523.37(m) c$^{-1}$;
F-19 NMR (ppm vs CFCl$_3$; 10% CDCL$_3$) Chemical Shifts:

OCF$_2$: $-72.97$ ppm (t of t; 4F; J$_{FF}$=4.88 Hz; J$_{FH}$=19.75 Hz)

H-1 NMR (CDCl$_3$ ppm): CH$_2$: 2.82 ppm (t; 2H; J$_{FH}$=19.70 Hz)

The yield of these materials is quite good. Surprising robustness of the hydryl-F-oxetane compounds to 10% NaOH at 75° C. has been demonstrated.

Comparison of the compounds to widely used CFC's R-113 and R-11 illustrates that they will be important replacement for those materials. Thus, the oxetanes of this invention will serve as replacement refrigerants. The oxetanes of this invention will also serve as highly useful solvents, alone or in solvent systems composed of combinations of these oxetanes with, for example, alcohols, turpenes or aqueous components. Significant comparative values are as follows:

| Compound | T$_a$ | T$_b$ | T$_c$ | ΔH$_{vap}$ |
|---|---|---|---|---|
| cy-CF$_2$CFHCF$_2$—O— | $-95°$ C. | 3.4° C. | 136.2° C. | 177.9 kJ/kg |
| cy-CF$_2$CH$_2$CF$_2$—O— | $-50°$ C. | 21.2° C. | 166.7° C. | 205.6 kJ/kg |
| R-114, CF$_2$ClCF$_2$Cl | $-94°$ C. | 3.77° C. | 145.7° C. | 136.02 kJ/kg |
| R-11, CFCl$_3$ | $-111°$ C. | 23.82° C. | 198° C. | 280.33 kJ/kg |

"wherein;

T$_m$ means melting point temperature,
T$_b$ means normal boiling point temperature,
T$_c$ means critical temperature at critical pressure, and
ΔH$_{vap}$ means the heat of vaporization."

What is claimed is:

1. A fluorinated oxetane having the structure: cyclo-CF$_2$CFHCF$_2$—O—.

2. A fluorinated oxetane having the structure: cyclo-CF$_2$CH$_2$CF$_2$—O—.

3. A solvent system comprising the oxetane of claim 1 or 2.

* * * * *

UNITED STATES PATENT AND TRADEMARK OFFICE
CERTIFICATE OF CORRECTION

PATENT NO. : 5,248,795
DATED : September 28, 1993
INVENTOR(S) : James L. Adcock

It is certified that error appears in the above-indentified patent and that said Letters Patent is hereby corrected as shown below:

Column 1, line 34 "fluorinated" should be --Fluorinated--.

Column 1, line 60, "supported" should be --suggested--.

Column 3, line 58, "9°C" should read -- -9°C--.

Column 4, line 64, "Temp. of Reactor Module #2: -9°C" should read --Temp. of Reactor Module #1: -10°C"--.

Column 5, line 5, "131°C" should read -- -131°C--.

Column 5, line 21, "4.5°" should read --4.5"--.

Column 5, line 31, "3-hydroyl-F" should read --3-hydryl-F--.

UNITED STATES PATENT AND TRADEMARK OFFICE
CERTIFICATE OF CORRECTION

PATENT NO. : 5,248,795

DATED : September 28, 1993

INVENTOR(S) : James L. Adcock

It is certified that error appears in the above-indentified patent and that said Letters Patent is hereby corrected as shown below:

Column 5, line 39, "3021 75" should read --3021.75--.

Column 6, line 3, "were used the" should read --were used when the--.

Column 6, line 5, "4.5°" should read --4.5"--.

Signed and Sealed this

Twelfth Day of July, 1994

Attest:

BRUCE LEHMAN

Attesting Officer

Commissioner of Patents and Trademarks